(12) United States Patent
Bigley et al.

(10) Patent No.: US 8,747,400 B2
(45) Date of Patent: *Jun. 10, 2014

(54) SYSTEMS AND METHODS FOR SCREEN ELECTRODE SECUREMENT

(75) Inventors: Robert Bigley, Redwood City, CA (US); Duane W. Marion, Santa Clara, CA (US)

(73) Assignee: ArthroCare Corporation, Austin, TX (US)

( * ) Notice: Subject to any disclaimer, the term of this patent is extended or adjusted under 35 U.S.C. 154(b) by 1371 days.

This patent is subject to a terminal disclaimer.

(21) Appl. No.: 12/190,752

(22) Filed: Aug. 13, 2008

(65) Prior Publication Data

US 2010/0042095 A1 Feb. 18, 2010

(51) Int. Cl.
*A61B 18/14* (2006.01)
*A61B 18/00* (2006.01)

(52) U.S. Cl.
CPC ....... *A61B 18/14* (2013.01); *A61B 2018/00625* (2013.01); *A61B 2018/1495* (2013.01); *A61B 2018/1497* (2013.01); *A61B 2218/007* (2013.01)
USPC ........................................................ 606/41

(58) Field of Classification Search
CPC ...... A61B 18/042; A61B 18/12; A61B 18/14; A61B 18/148; A61B 2018/00077; A61B 2018/00577; A61B 2018/00583; A61B 2018/00589; A61B 2018/00601; A61B 2018/00607; A61B 2018/00625; A61B 2018/0063; A61B 2018/1467; A61B 2018/1495; A61B 2018/1497; A61B 2018/162; A61B 2218/007
USPC ......... 606/40, 41; 600/372, 373, 393; 607/98, 607/155
See application file for complete search history.

(56) References Cited

U.S. PATENT DOCUMENTS

| | | | |
|---|---|---|---|
| 2,050,904 A | 8/1936 | Trice | 219/233 |
| 2,056,377 A | 10/1939 | Wappler | 125/303 |
| 2,275,167 A | 3/1942 | Bierman | 606/50 |
| 3,633,425 A | 1/1972 | Sanford | 73/356 |

(Continued)

FOREIGN PATENT DOCUMENTS

| | | | |
|---|---|---|---|
| DE | 2521719 | 11/1976 | A61N 3/02 |
| DE | 3930451 A1 | 3/1991 | A61B 17/39 |

(Continued)

OTHER PUBLICATIONS

EP Search Report for EP 03736488 3 pgs, Mailed Jun. 25, 2009.

(Continued)

*Primary Examiner* — Michael Peffley
*Assistant Examiner* — Thomas Giuliani
(74) *Attorney, Agent, or Firm* — Matthew Scheele; Brian E. Szymczak

(57) ABSTRACT

Systems and methods for securing a screen-type active electrode to the distal tip of an electrosurgical device used for selectively applying electrical energy to a target location within or on a patient's body. A securing electrode is disposed through the screen electrode and mechanically joined to an insulative support body while also creating an electrical connection and mechanical engagement with the screen electrode. The electrosurgical device and related methods are provided for resecting, cutting, partially ablating, aspirating or otherwise removing tissue from a target site, and ablating the tissue in situ. The present methods and systems are particularly useful for removing tissue within joints, e.g., synovial tissue, meniscus, articular cartilage and the like.

15 Claims, 7 Drawing Sheets

(56) References Cited

U.S. PATENT DOCUMENTS

| | | | |
|---|---|---|---|
| 3,699,967 A | 10/1972 | Anderson | 606/37 |
| 3,812,858 A | 5/1974 | Oringer | 604/22 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,945,375 A | 3/1976 | Banko | 600/104 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 606/15 |
| 4,202,337 A | 5/1980 | Hren et al. | 128/303 |
| 4,203,444 A | 5/1980 | Bonnell et al. | 604/22 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 128/692 |
| 4,248,231 A | 2/1981 | Herczog et al. | 128/303 |
| 4,269,174 A | 5/1981 | Adair | 128/842 |
| 4,326,529 A | 4/1982 | Doss et al. | 128/303 |
| 4,381,007 A | 4/1983 | Doss | 128/303 |
| 4,411,266 A | 10/1983 | Cosman | 606/49 |
| 4,429,694 A | 2/1984 | McGreevy | 128/303.14 |
| 4,474,179 A | 10/1984 | Koch | 606/40 |
| 4,476,862 A | 10/1984 | Pao | 128/303 |
| 4,483,338 A | 11/1984 | Bloom et al. | 606/50 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,582,057 A | 4/1986 | Auth et al. | 606/31 |
| 4,590,934 A | 5/1986 | Malis et al. | 128/303 |
| 4,593,691 A | 6/1986 | Lindstrom et al. | 128/303 |
| 4,641,649 A | 2/1987 | Walinsky | 606/33 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 128/303 |
| 4,719,914 A | 1/1988 | Johnson | 606/28 |
| 4,727,874 A | 3/1988 | Bowers et al. | 128/303 |
| 4,736,743 A | 4/1988 | Daikuzono | 128/303.1 |
| 4,737,678 A | 4/1988 | Hasegawa | 313/36 |
| 4,762,128 A | 8/1988 | Rosenbluth | 128/343 |
| 4,765,331 A | 8/1988 | Petruzzi et al. | 128/303 |
| 4,785,806 A | 11/1988 | Deckelbaum | 128/303.1 |
| 4,785,823 A | 11/1988 | Eggers et al. | 128/692 |
| 4,805,616 A | 2/1989 | Pao | 128/303 |
| 4,813,429 A | 3/1989 | Eshel et al. | 128/736 |
| 4,823,791 A | 4/1989 | D'Amelio et al. | 123/303 |
| 4,827,911 A | 5/1989 | Broadwin et al. | 604/22 |
| 4,832,048 A | 5/1989 | Cohen | 128/786 |
| 4,860,752 A | 8/1989 | Turner et al. | 128/422 |
| 4,903,696 A | 2/1990 | Stasz et al. | 606/37 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,940,064 A | 7/1990 | Desai | 607/122 |
| 4,943,290 A | 7/1990 | Rexroth et al. | 606/45 |
| 4,955,377 A | 9/1990 | Lennox et al. | 128/401 |
| 4,966,597 A | 10/1990 | Cosman | 606/50 |
| 4,967,765 A | 11/1990 | Turner et al. | 128/785 |
| 4,968,314 A | 11/1990 | Michaels | 606/7 |
| 4,976,709 A | 12/1990 | Sand | 606/5 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,437 A | 4/1991 | Sterzer | 428/786 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,037,421 A | 8/1991 | Boutacoff et al. | 606/15 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,061,266 A | 10/1991 | Hakky | 606/15 |
| 5,078,717 A | 1/1992 | Parins et al. | 606/48 |
| 5,080,660 A | 1/1992 | Buelna | 606/45 |
| 5,083,565 A | 1/1992 | Parins | 128/642 |
| 5,084,044 A | 1/1992 | Quint | 606/27 |
| 5,084,045 A | 1/1992 | Helenowski | 606/32 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 128/692 |
| 5,093,877 A | 3/1992 | Aita et al. | 385/34 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,103,804 A | 4/1992 | Abele et al. | 600/116 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,137,530 A | 8/1992 | Sand | 606/5 |
| 5,147,354 A | 9/1992 | Boutacoff et al. | 606/15 |
| 5,151,098 A | 9/1992 | Loertscher | 606/16 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,176,528 A | 1/1993 | Fry et al. | 439/181 |
| 5,178,620 A | 1/1993 | Eggers et al. | 606/41 |
| 5,190,517 A | 3/1993 | Zieve et al. | 604/22 |
| 5,191,883 A | 3/1993 | Lennox et al. | 607/102 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,455 A | 6/1993 | Tan | 606/9 |
| 5,217,457 A | 6/1993 | Delahuerga et al. | 606/42 |
| 5,217,459 A | 6/1993 | Kamerling | 606/48 |
| 5,230,334 A | 7/1993 | Klopotek | 601/3 |
| 5,234,428 A | 8/1993 | Kaufman | 606/45 |
| 5,246,438 A | 9/1993 | Langberg | 606/33 |
| 5,249,585 A | 10/1993 | Turner et al. | 607/99 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,269,794 A | 12/1993 | Rexroth | 606/180 |
| 5,273,524 A | 12/1993 | Fox et al. | 604/21 |
| 5,277,201 A | 1/1994 | Stern | 607/98 |
| 5,277,696 A | 1/1994 | Hagen | 606/49 |
| 5,279,299 A | 1/1994 | Imran | 600/393 |
| 5,281,216 A | 1/1994 | Klicek | 606/42 |
| 5,281,218 A | 1/1994 | Imran | 606/41 |
| 5,282,797 A | 2/1994 | Chess | 606/9 |
| 5,282,799 A | 2/1994 | Rydell | 606/48 |
| 5,290,273 A | 3/1994 | Tan | 606/9 |
| 5,290,282 A | 3/1994 | Casscells | 606/29 |
| 5,293,868 A | 3/1994 | Nardella | 600/373 |
| 5,295,956 A | 3/1994 | Bales et al. | 604/30 |
| 5,300,069 A | 4/1994 | Hunsberger et al. | 606/37 |
| 5,300,099 A | 4/1994 | Rudie | 607/101 |
| 5,301,687 A | 4/1994 | Wong et al. | 607/116 |
| 5,304,169 A | 4/1994 | Sand | 606/5 |
| 5,304,170 A | 4/1994 | Green | 606/9 |
| 5,306,238 A | 4/1994 | Fleenor | 606/42 |
| 5,312,395 A | 5/1994 | Tan et al. | 606/9 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,322,507 A | 6/1994 | Costello et al. | 128/4 |
| 5,324,254 A | 6/1994 | Phillips | 604/21 |
| 5,330,470 A | 7/1994 | Hagen | 606/42 |
| 5,330,518 A | 7/1994 | Neilson et al. | 607/101 |

(56) References Cited

U.S. PATENT DOCUMENTS

| | | | |
|---|---|---|---|
| 5,334,140 A | 8/1994 | Phillips | 604/35 |
| 5,334,183 A | 8/1994 | Wuchinich | 606/46 |
| 5,334,193 A | 8/1994 | Nardella | 606/41 |
| 5,335,668 A | 8/1994 | Nardella | 600/547 |
| 5,336,217 A | 8/1994 | Buys et al. | 606/9 |
| 5,336,220 A | 8/1994 | Ryan et al. | 604/22 |
| 5,342,357 A | 8/1994 | Nardella | 606/40 |
| 5,348,554 A | 9/1994 | Imran et al. | 606/41 |
| 5,366,443 A | 11/1994 | Eggers | 252/511 |
| 5,370,642 A | 12/1994 | Keller | 606/9 |
| 5,370,644 A | 12/1994 | Langberg | 606/33 |
| 5,370,675 A | 12/1994 | Edwards et al. | 607/101 |
| 5,374,261 A | 12/1994 | Yoon | 604/385.01 |
| 5,374,265 A | 12/1994 | Sand | 606/5 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,395,363 A | 3/1995 | Billings et al. | 606/41 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,405,376 A | 4/1995 | Mulier et al. | 607/127 |
| 5,417,687 A | 5/1995 | Nardella et al. | 606/32 |
| 5,419,767 A | 5/1995 | Eggers et al. | 604/114 |
| 5,423,803 A | 6/1995 | Tankovich | 606/9 |
| 5,423,810 A | 6/1995 | Goble et al. | 606/40 |
| 5,423,844 A | 6/1995 | Miller | 606/171 |
| 5,423,882 A | 6/1995 | Jackman et al. | 607/122 |
| 5,431,649 A | 7/1995 | Mulier et al. | 606/41 |
| 5,433,708 A | 7/1995 | Nichols et al. | 604/113 |
| 5,436,566 A | 7/1995 | Thompson et al. | 324/713 |
| 5,437,662 A | 8/1995 | Nardella | 606/40 |
| 5,437,664 A | 8/1995 | Cohen et al. | 606/42 |
| 5,438,302 A | 8/1995 | Goble | 331/167 |
| 5,441,499 A | 8/1995 | Fritzsch | 606/45 |
| 5,445,634 A | 8/1995 | Keller | 606/9 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,462,545 A | 10/1995 | Wang et al. | 606/41 |
| 5,484,435 A | 1/1996 | Fleenor et al. | 606/46 |
| 5,487,385 A | 1/1996 | Avitall | 600/374 |
| 5,490,850 A | 2/1996 | Ellman et al. | 606/45 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,710 A | 4/1996 | Dorsey, III | 604/158 |
| 5,514,130 A | 5/1996 | Baker | 606/41 |
| 5,520,685 A | 5/1996 | Wojciechowicz | 606/49 |
| 5,536,267 A | 7/1996 | Edwards et al. | 606/41 |
| 5,542,928 A | 8/1996 | Evans et al. | 604/113 |
| 5,545,161 A | 8/1996 | Imran | 606/41 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,567,890 A | 10/1996 | Lindberg et al. | 75/243 |
| 5,569,242 A | 10/1996 | Lax et al. | 606/42 |
| 5,571,100 A | 11/1996 | Goble et al. | 606/41 |
| 5,579,764 A | 12/1996 | Goldreyer | 600/374 |
| 5,584,872 A | 12/1996 | LaFontaine et al. | 607/117 |
| 5,607,421 A | 3/1997 | Jeevanandam et al. | 606/15 |
| 5,609,151 A | 3/1997 | Mulier et al. | 128/642 |
| 5,626,576 A | 5/1997 | Janssen | 606/41 |
| 5,633,578 A | 5/1997 | Eggers et al. | 323/301 |
| 5,643,255 A | 7/1997 | Organ | 606/41 |
| 5,647,869 A | 7/1997 | Goble et al. | 606/37 |
| 5,653,692 A | 8/1997 | Masterson et al. | 604/113 |
| 5,660,836 A | 8/1997 | Knowlton | 607/101 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,681,308 A | 10/1997 | Edwards et al. | 606/41 |
| 5,683,366 A | 11/1997 | Eggers et al. | 604/114 |
| 5,688,267 A | 11/1997 | Panescu et al. | 606/41 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,713,896 A | 2/1998 | Nardella | 606/50 |
| 5,725,524 A | 3/1998 | Mulier et al. | 606/41 |
| 5,743,870 A | 4/1998 | Edwards | 604/22 |
| 5,743,903 A | 4/1998 | Stern et al. | 606/31 |
| 5,746,746 A | 5/1998 | Garito et al. | 606/41 |
| 5,749,869 A | 5/1998 | Lindenmeier et al. | 606/34 |
| 5,755,753 A | 5/1998 | Knowlton | 607/98 |
| 5,766,153 A | 6/1998 | Eggers et al. | 604/114 |
| 5,769,843 A | 6/1998 | Abela et al. | 606/10 |
| 5,769,847 A | 6/1998 | Panescu et al. | 606/42 |
| 5,782,795 A | 7/1998 | Bays | 604/22 |
| 5,785,705 A | 7/1998 | Baker | 606/32 |
| 5,800,429 A | 9/1998 | Edwards | 606/41 |
| 5,800,431 A | 9/1998 | Brown | 606/42 |
| 5,807,384 A | 9/1998 | Mueller | 606/7 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,843,019 A | 12/1998 | Eggers et al. | 604/22 |
| 5,843,078 A | 12/1998 | Sharkey | 606/41 |
| 5,855,277 A | 1/1999 | Apps et al. | 606/35 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,871,524 A | 2/1999 | Knowlton | 607/101 |
| 5,873,855 A | 2/1999 | Eggers et al. | 604/114 |
| 5,876,398 A | 3/1999 | Mulier et al. | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,893,848 A | 4/1999 | Negus et al. | 606/41 |
| 5,895,386 A | 4/1999 | Odell et al. | 606/50 |
| 5,897,553 A | 4/1999 | Mulier | 606/41 |
| 5,902,272 A | 5/1999 | Eggers et al. | 604/114 |
| 5,904,681 A | 5/1999 | West, Jr. | 606/41 |
| 5,906,613 A | 5/1999 | Mulier et al. | 606/41 |
| 5,919,219 A | 7/1999 | Knowlton | 607/102 |
| 5,944,715 A | 8/1999 | Goble et al. | 606/41 |
| 5,954,716 A | 9/1999 | Sharkey et al. | 606/32 |
| 5,964,754 A | 10/1999 | Osypka | 606/37 |
| 5,976,127 A | 11/1999 | Lax | 606/32 |
| 5,980,516 A | 11/1999 | Mulier et al. | 606/41 |
| 5,980,545 A | 11/1999 | Pacala et al. | 606/170 |
| 5,984,919 A | 11/1999 | Hilal et al. | 606/45 |
| 6,004,319 A | 12/1999 | Goble et al. | 606/48 |
| 6,007,533 A | 12/1999 | Casscells et al. | 606/45 |
| 6,007,570 A | 12/1999 | Sharkey et al. | 607/96 |
| 6,013,076 A | 1/2000 | Goble et al. | 606/41 |
| 6,015,406 A | 1/2000 | Goble et al. | 606/41 |
| 6,016,809 A | 1/2000 | Mulier et al. | 128/898 |
| 6,024,733 A | 2/2000 | Eggers et al. | 604/500 |
| 6,027,501 A | 2/2000 | Goble et al. | 606/41 |
| 6,030,383 A | 2/2000 | Benderev | 606/45 |
| 6,032,673 A | 3/2000 | Savage et al. | 128/898 |
| 6,032,674 A | 3/2000 | Eggers et al. | 606/41 |
| 6,039,734 A | 3/2000 | Goble et al. | 606/41 |
| 6,042,580 A | 3/2000 | Simpson | 606/32 |
| 6,045,532 A | 4/2000 | Eggers et al. | 604/114 |
| 6,047,700 A | 4/2000 | Eggers et al. | 128/898 |
| 6,053,172 A | 4/2000 | Hovda et al. | 128/898 |
| 6,056,746 A | 5/2000 | Goble et al. | 606/48 |
| 6,063,079 A | 5/2000 | Hovda et al. | 606/41 |
| 6,063,081 A | 5/2000 | Mulier et al. | 606/45 |
| 6,066,134 A | 5/2000 | Eggers et al. | 606/32 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |

(56) References Cited

U.S. PATENT DOCUMENTS

| | | | |
|---|---|---|---|
| 6,091,995 A | 7/2000 | Ingle et al. | 607/138 |
| 6,093,186 A | 7/2000 | Goble et al. | 606/34 |
| 6,096,037 A | 8/2000 | Mulier et al. | 606/49 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,110,169 A | 8/2000 | Mueller et al. | 606/48 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 4/22 |
| 6,152,923 A | 11/2000 | Ryan | 606/51 |
| 6,156,031 A | 12/2000 | Aita et al. | 606/33 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,214,001 B1 | 4/2001 | Casscells et al. | 606/41 |
| 6,217,575 B1 | 4/2001 | DeVore et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,235,020 B1 | 5/2001 | Cheng et al. | 606/34 |
| 6,235,023 B1 | 5/2001 | Lee et al. | 606/41 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 607/127 |
| 6,254,600 B1 | 7/2001 | Willink et al. | 606/41 |
| 6,261,286 B1 | 7/2001 | Goble et al. | 606/34 |
| 6,261,311 B1 | 7/2001 | Sharkey et al. | 607/96 |
| 6,264,650 B1 | 7/2001 | Hovda | 606/32 |
| 6,264,652 B1 | 7/2001 | Eggers et al. | 606/41 |
| 6,267,757 B1 | 7/2001 | Aita et al. | 606/33 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 606/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,302,903 B1 | 10/2001 | Mulier et al. | 607/105 |
| 6,306,134 B1 | 10/2001 | Goble et al. | 606/42 |
| 6,308,089 B1 | 10/2001 | von der Ruhr et al. | 600/338 |
| 6,309,387 B1 | 10/2001 | Eggers et al. | 606/41 |
| 6,312,408 B1 | 11/2001 | Eggers et al. | 604/114 |
| 6,312,429 B1 | 11/2001 | Butbank et al. | 606/47 |
| 6,315,774 B1 | 11/2001 | Daniel et al. | 606/15 |
| 6,322,494 B1 | 11/2001 | Bullivant et al. | 600/104 |
| 6,322,549 B1 | 11/2001 | Eggers et al. | 604/500 |
| 6,325,799 B1 | 12/2001 | Goble | 606/41 |
| 6,327,505 B1 | 12/2001 | Medhkour et al. | 607/99 |
| 6,328,736 B1 | 12/2001 | Mulier et al. | 606/45 |
| 6,336,926 B1 | 1/2002 | Goble | 606/34 |
| 6,346,107 B1 | 2/2002 | Cucin | 606/49 |
| 6,355,006 B1 | 3/2002 | Ryaby et al. | 601/2 |
| 6,355,032 B1 | 3/2002 | Hovda et al. | 606/32 |
| 6,358,248 B1 | 3/2002 | Mulier et al. | 606/41 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |
| 6,379,351 B1 | 4/2002 | Thapliyal et al. | 606/41 |
| 6,391,025 B1 | 5/2002 | Weinstein et al. | 606/41 |
| 6,391,028 B1 | 5/2002 | Fanton et al. | 606/45 |
| 6,398,781 B1 | 6/2002 | Goble et al. | 606/41 |
| 6,409,724 B1 | 6/2002 | Penny et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,432,103 B1 | 8/2002 | Ellsberry et al. | 606/41 |
| 6,432,105 B1 * | 8/2002 | Ellman et al. | 606/48 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,482,202 B1 | 11/2002 | Goble et al. | 606/41 |
| 6,491,690 B1 | 12/2002 | Gobel et al. | 606/41 |
| 6,497,705 B2 | 12/2002 | Comben | 606/41 |
| 6,497,706 B1 | 12/2002 | Burbank et al. | 606/45 |
| 6,510,854 B2 | 1/2003 | Gobel | 128/898 |
| 6,514,250 B1 | 2/2003 | Jahns et al. | 606/41 |
| 6,517,498 B1 | 2/2003 | Burbank et al. | 600/564 |
| 6,517,535 B2 | 2/2003 | Edwards | 606/41 |
| 6,530,922 B2 | 3/2003 | Cosman | 606/34 |
| 6,540,741 B1 | 4/2003 | Underwood et al. | 606/32 |
| 6,557,559 B1 | 5/2003 | Eggers et al. | 128/898 |
| 6,575,968 B1 | 6/2003 | Eggers et al. | 606/41 |
| 6,575,969 B1 | 6/2003 | Rittman, III et al. | 606/41 |
| 6,578,579 B2 | 6/2003 | Burnside | 128/897 |
| 6,582,423 B1 | 6/2003 | Thapliyal et al. | 606/32 |
| 6,589,237 B2 | 7/2003 | Woloszko et al. | 606/41 |
| 6,595,990 B1 | 7/2003 | Weinstein et al. | 606/41 |
| 6,597,950 B2 | 7/2003 | Linder et al. | 607/8 |
| 6,605,085 B1 | 8/2003 | Edwards | 606/41 |
| 6,610,059 B1 | 8/2003 | West, Jr. | 606/41 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,632,230 B2 | 10/2003 | Barry | 606/159 |
| 6,663,628 B2 | 12/2003 | Peters | 606/45 |
| 6,695,839 B2 | 2/2004 | Sharkey et al. | 606/49 |
| 6,699,206 B2 | 3/2004 | Burbank et al. | 606/567 |
| 6,699,244 B2 | 3/2004 | Carranza et al. | 606/41 |
| 6,702,810 B2 | 3/2004 | McClurken et al. | 606/34 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| 6,763,836 B2 | 7/2004 | Tasto et al. | 128/898 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,796,982 B2 | 9/2004 | Carmel et al. | 606/41 |
| 6,802,842 B2 | 10/2004 | Ellman et al. | 606/45 |
| 6,805,130 B2 | 10/2004 | Tasto et al. | 606/32 |
| 6,827,725 B2 | 12/2004 | Batchelor et al. | 606/170 |
| 6,832,996 B2 | 12/2004 | Woloszko et al. | 606/41 |
| 6,837,887 B2 | 1/2005 | Woloszko et al. | 606/41 |
| 6,837,888 B2 | 1/2005 | Ciarrocca et al. | 606/41 |
| 6,855,143 B2 | 2/2005 | Davison et al. | 606/41 |
| 6,896,674 B1 | 5/2005 | Woloszko et al. | 606/41 |
| 6,904,303 B2 | 6/2005 | Phan et al. | 600/374 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,979,332 B2 | 12/2005 | Adams | 606/45 |
| 6,984,231 B2 | 1/2006 | Goble et al. | 606/37 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 7,150,747 B1 | 12/2006 | McDonald et al. | 606/45 |
| 7,169,143 B2 | 1/2007 | Eggers et al. | 606/32 |
| 7,179,255 B2 | 2/2007 | Lettice et al. | 606/32 |
| 7,184,811 B2 | 2/2007 | Phan et al. | 600/374 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 * | 7/2007 | Davison | 606/41 |
| 7,258,690 B2 | 8/2007 | Sutton et al. | 606/45 |
| 7,261,712 B2 | 8/2007 | Burbank et al. | 606/49 |
| 7,270,658 B2 | 9/2007 | Woloszko et al. | 606/32 |
| 7,270,659 B2 | 9/2007 | Hovda et al. | 606/32 |

(56) References Cited

U.S. PATENT DOCUMENTS

| | | |
|---|---|---|
| 7,270,661 B2 | 9/2007 | Dahla et al. ............... 606/41 |
| 7,276,063 B2 | 10/2007 | Davison et al. ............ 606/45 |
| 7,297,143 B2 | 11/2007 | Woloszko et al. .......... 606/41 |
| 7,297,145 B2 | 11/2007 | Ormsby et al. ............. 606/41 |
| 7,318,823 B2 | 1/2008 | Sharps et al. .............. 606/32 |
| 7,331,956 B2 | 2/2008 | Hovda et al. .............. 606/32 |
| RE40,156 E | 3/2008 | Sharps et al. .............. 606/32 |
| 7,357,798 B2 | 4/2008 | Sharps et al. .............. 606/32 |
| 7,387,625 B2 | 6/2008 | Hovda et al. .............. 606/32 |
| 7,419,488 B2 | 9/2008 | Ciarrocca et al. .......... 606/41 |
| 7,429,260 B2 | 9/2008 | Underwood et al. ....... 606/32 |
| 7,429,262 B2 | 9/2008 | Woloszko et al. .......... 606/48 |
| 7,435,247 B2 | 10/2008 | Woloszko et al. .......... 604/45 |
| 7,488,295 B2 | 2/2009 | Burbank et al. ........... 606/167 |
| 7,776,034 B2 | 8/2010 | Kampa ........................ 606/41 |
| 7,819,863 B2 | 10/2010 | Eggers et al. .............. 606/32 |
| 8,038,670 B2 | 10/2011 | McClurken ................. 606/41 |
| 2001/0023347 A1* | 9/2001 | Sharkey et al. ............. 606/41 |
| 2001/0025177 A1 | 9/2001 | Woloszko et al. .......... 606/46 |
| 2002/0029036 A1 | 3/2002 | Goble et al. ................ 606/38 |
| 2002/0049438 A1* | 4/2002 | Sharkey et al. ............. 606/41 |
| 2002/0072739 A1 | 6/2002 | Lee et al. .................... 606/47 |
| 2003/0013986 A1 | 1/2003 | Saadat ........................ 600/549 |
| 2003/0028189 A1 | 2/2003 | Woloszko et al. .......... 604/45 |
| 2003/0088245 A1 | 5/2003 | Woloszko et al. .......... 606/41 |
| 2003/0130711 A1 | 7/2003 | Pearson et al. ............. 607/101 |
| 2003/0158545 A1 | 8/2003 | Hovda et al. .............. 606/32 |
| 2003/0171743 A1 | 9/2003 | Tasto et al. .................. 3/32 |
| 2003/0208194 A1 | 11/2003 | Hovda et al. .............. 606/41 |
| 2003/0208196 A1 | 11/2003 | Stone ........................ 606/41 |
| 2003/0212396 A1 | 11/2003 | Eggers et al. .............. 606/41 |
| 2004/0116922 A1 | 6/2004 | Hovda et al. .............. 606/41 |
| 2004/0127893 A1 | 7/2004 | Hovda ........................ 606/41 |
| 2004/0230190 A1 | 11/2004 | Dahla et al. ................ 604/41 |
| 2005/0004634 A1 | 1/2005 | Hovda et al. .............. 606/41 |
| 2005/0119650 A1 | 6/2005 | Sanders et al. ............. 424/426 |
| 2005/0131402 A1 | 6/2005 | Ciarrocca et al. .......... 600/450 |
| 2005/0187543 A1 | 8/2005 | Underwood et al. ....... 606/41 |
| 2005/0234439 A1 | 10/2005 | Underwood et al. ....... 606/32 |
| 2005/0251134 A1 | 11/2005 | Woloszko et al. .......... 606/32 |
| 2005/0261754 A1 | 11/2005 | Woloszko et al. .......... 606/32 |
| 2005/0288665 A1 | 12/2005 | Woloszko et al. .......... 606/41 |
| 2006/0036237 A1 | 2/2006 | Davison et al. ............ 606/41 |
| 2006/0095031 A1 | 5/2006 | Ormsby ...................... 606/34 |
| 2006/0178670 A1 | 8/2006 | Woloszko et al. .......... 606/48 |
| 2006/0189971 A1 | 8/2006 | Eggers et al. .............. 606/32 |
| 2006/0253117 A1 | 11/2006 | Hovda et al. .............. 128/898 |
| 2006/0259025 A1 | 11/2006 | Dahla ........................ 607/108 |
| 2007/0010808 A1 | 1/2007 | Dahla ........................ 606/41 |
| 2007/0106288 A1 | 5/2007 | Woloszko et al. .......... 606/41 |
| 2007/0112348 A1 | 5/2007 | Eggers et al. .............. 606/41 |
| 2007/0129715 A1 | 6/2007 | Eggers et al. .............. 606/32 |
| 2007/0149966 A1 | 6/2007 | Dahla et al. ................ 606/41 |
| 2007/0161981 A1 | 7/2007 | Sanders et al. ............. 606/41 |
| 2007/0179497 A1 | 8/2007 | Eggers et al. .............. 606/41 |
| 2007/0208334 A1 | 9/2007 | Woloszko et al. .......... 606/41 |
| 2007/0208335 A1 | 9/2007 | Woloszko et al. .......... 606/41 |
| 2007/0213700 A1 | 9/2007 | Davison et al. ............ 606/32 |
| 2007/0282323 A1 | 12/2007 | Woloszko et al. .......... 606/41 |
| 2008/0021447 A1 | 1/2008 | Davison et al. ............ 606/41 |
| 2008/0167645 A1 | 7/2008 | Woloszko .................... 606/40 |
| 2008/0167646 A1 | 7/2008 | Godara et al. .............. 606/41 |
| 2008/0234673 A1 | 9/2008 | Marion et al. .............. 606/45 |
| 2008/0300590 A1 | 12/2008 | Horne et al. ................ 606/35 |
| 2009/0069807 A1 | 3/2009 | Eggers et al. .............. 606/48 |
| 2009/0138011 A1 | 5/2009 | Epstein ...................... 606/42 |
| 2009/0209958 A1 | 8/2009 | Davison et al. ............ 606/41 |
| 2010/0152724 A1 | 6/2010 | Marion et al. .............. 606/41 |
| 2010/0204690 A1* | 8/2010 | Bigley et al. ............... 606/41 |
| 2011/0077643 A1 | 3/2011 | Dahla et al. ................ 606/41 |
| 2011/0077646 A1 | 3/2011 | Dahla et al. ................ 606/50 |
| 2011/0270242 A1 | 11/2011 | Marion ...................... 606/35 |

FOREIGN PATENT DOCUMENTS

| | | | |
|---|---|---|---|
| DE | 4425015 | 1/1996 | A61B 17/36 |
| DE | 296 09 350 | 8/1996 | A61B 17/39 |
| DE | 195 37 084 | 4/1997 | A61B 17/36 |
| DE | 296 19 029 | 4/1997 | A61B 17/34 |
| DE | 19850671 | 5/1999 | A61B 17/22 |
| DE | 10254668 | 6/2004 | A61B 18/12 |
| DE | 69822877 | 1/2005 | A61B 17/20 |
| DE | 202008000276 | 6/2008 | A61B 18/12 |
| DE | 102009057921 A1 | 6/2010 | A61B 18/12 |
| EP | 0 502 268 | 9/1992 | A61B 17/39 |
| EP | 0 515 867 | 12/1992 | A61B 17/36 |
| EP | 543123 | 5/1993 | A61B 17/39 |
| EP | 0 597 463 | 5/1994 | A61N 5/04 |
| EP | 774926 | 3/1995 | A61B 17/39 |
| EP | 0 650 701 | 5/1995 | A61B 17/39 |
| EP | 0703461 A2 | 3/1996 | G01B 27/02 |
| EP | 0740926 A2 | 11/1996 | A61B 17/39 |
| EP | 0 754 437 | 1/1997 | A61B 17/39 |
| EP | 923907 | 6/1999 | A61B 17/39 |
| EP | 0 694 290 | 11/2000 | A61B 18/04 |
| EP | 1149564 | 10/2001 | A61B 18/14 |
| EP | 1041933 | 3/2004 | A61B 17/20 |
| FR | 2313949 | 1/1977 | A61N 3/02 |
| GB | 2037167 | 7/1980 | A61B 17/36 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2331247 | 5/1999 | A61B 17/39 |
| GB | 2379878 | 3/2003 | A61B 18/04 |
| GB | 2408936 | 6/2005 | A61B 18/14 |
| JP | 57-57802 | 4/1982 | A61B 1/00 |
| JP | 57-117843 | 7/1982 | A61B 17/39 |
| JP | 57-183850 | 11/1982 | A61F 9/00 |
| JP | 63-40099 | 8/1988 | A61B 17/39 |
| JP | 9-501328 | 2/1997 | A61B 17/39 |
| WO | 90/03152 | 4/1990 | A61B 17/39 |
| WO | 90/07303 | 7/1990 | A61B 17/39 |
| WO | 91/13650 | 9/1991 | A61N 5/04 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/03134 | 2/1994 | A61B 18/20 |
| WO | 94/04220 | 3/1994 | |
| WO | 94/08654 | 4/1994 | A61M 37/00 |
| WO | 94/10924 | 5/1994 | A61B 17/39 |
| WO | 94/14383 | 7/1994 | A61B 17/36 |
| WO | 94/26228 | 11/1994 | A61G 17/36 |
| WO | 95/05780 | 3/1995 | A61B 17/36 |
| WO | 95/05781 | 3/1995 | A61B 17/39 |
| WO | 95/05867 | 3/1995 | A61N 1/05 |
| WO | 95/10326 | 4/1995 | A61N 5/00 |
| WO | 95/30373 | 11/1995 | A61B 17/00 |
| WO | 95/34259 | 12/1995 | A61F 5/48 |
| WO | 96/00042 | 1/1996 | A61B 17/39 |
| WO | 96/07360 | 3/1996 | A61B 17/39 |
| WO | 96/34568 | 11/1996 | A61B 17/36 |
| WO | 96/35469 | 11/1996 | A61B 17/36 |
| WO | 96/39914 | 12/1996 | A61B 1/00 |
| WO | 96/39962 | 12/1996 | A61B 17/36 |
| WO | 96/39964 | 12/1996 | A61B 17/36 |
| WO | 96/39965 | 12/1996 | A61B 17/36 |
| WO | 96/39967 | 12/1996 | A61B 17/38 |
| WO | 97/00646 | 1/1997 | A61B 17/39 |
| WO | 97/00647 | 1/1997 | A61B 17/39 |
| WO | 97/15238 | 5/1997 | A61B 17/39 |
| WO | 97/18765 | 5/1997 | A61B 17/36 |
| WO | 97/24073 | 7/1997 | A61B 17/39 |
| WO | 97/24074 | 7/1997 | A61B 17/39 |
| WO | 97/24992 | 7/1997 | A61B 17/38 |
| WO | 97/24993 | 7/1997 | A61B 17/39 |
| WO | 97/24994 | 7/1997 | A61B 17/39 |
| WO | 97/25101 | 7/1997 | A61N 5/00 |
| WO | 97/32551 | 9/1997 | A61F 11/00 |
| WO | 97/33523 | 9/1997 | A61B 17/32 |

(56) References Cited

FOREIGN PATENT DOCUMENTS

| | | | |
|---|---|---|---|
| WO | 97/34540 | 9/1997 | A61B 17/36 |
| WO | 97/41786 | 11/1997 | A61B 17/39 |
| WO | 97/44071 | 11/1997 | A61M 1/10 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/14131 | 4/1998 | A61B 18/14 |
| WO | 98/17185 | 4/1998 | A61B 17/36 |
| WO | 98/17186 | 4/1998 | A61B 17/36 |
| WO | 98/27877 | 7/1998 | A61B 17/32 |
| WO | 98/27879 | 7/1998 | A61B 17/36 |
| WO | 98/27880 | 7/1998 | A61B 17/39 |
| WO | 98/30144 | 7/1998 | A61B 17/36 |
| WO | 98/34550 | 8/1998 | A61B 17/39 |
| WO | 98/34558 | 8/1998 | A61B 18/00 |
| WO | 98/38925 | 9/1998 | A61B 17/20 |
| WO | 98/39038 | 9/1998 | A61M 5/00 |
| WO | 99/00060 | 1/1999 | A61B 17/22 |
| WO | 99/20185 | 4/1999 | A61B 17/20 |
| WO | 99/42037 | 8/1999 | A61B 17/00 |
| WO | 99/44506 | 9/1999 | A61B 10/00 |
| WO | 99/51155 | 10/1999 | A61B 17/36 |
| WO | 99/51158 | 10/1999 | A61B 17/39 |
| WO | 00/09053 | 2/2000 | A61F 7/12 |
| WO | 01/26570 | 4/2001 | A61B 18/14 |
| WO | 01/87154 | 5/2001 | A61B 5/05 |
| WO | 01/95819 | 12/2001 | A61B 18/14 |
| WO | 02/36028 | 5/2002 | A61B 18/12 |
| WO | 02/078557 | 10/2002 | A61B 18/18 |
| WO | 03/024339 | 3/2003 | A61B 17/32 |
| WO | 2005/125287 | 12/2005 | A61B 18/00 |
| WO | 2008/073727 | 6/2008 | A61B 18/14 |
| WO | 2009/094392 | 7/2009 | A61B 18/14 |
| WO | 2011/071482 | 6/2011 | A61B 18/14 |

OTHER PUBLICATIONS

PCT International Search Report for PCT/US96/18505, 3 pgs, Mailed Jan. 17, 1997.
PCT Notif of the Int'l Search Report and Written Opinion for PCT/US09/67001 6 pgs, Mailed Jan. 29, 2010.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Hardy et al., "Regional Myocardial Blood Flow and Cardiac mechanics in dog Hearts with CO2 laser-induced Intramyocardial Revascularization", Basic Research in cardiology 85:179-196, 1990.
Mirhoseini et al., "New Concepts in Revascularization of the Myocardium", Ann Thorac Surg 45:415-420, 1988.
Mirhoseini et al., "Revascularization of the heart by Laser", J. of Microsurgery 2:253-260, 1981.
Mirhoseini et al., "Transmyocardial Laser Revascularization: A Review", J. of Clinical Laser medicine & Surgery 11 (1):15-19, 1993.
Mirhoseini et al., "Transventricular Revascularization by Laser", Lasers in Surgery and Medicine 2:187-198, 1982.
Rand et al., "Effect of Elecctrocautery on Fresh Human Articular Cartilage", J. Arthro. Surg., vol. 1, pp. 242-246, 1985.
Walter et al., "Treatment of Acute Mycardial Infarction by Transmural Blood Supply from the Ventricular Cavity", Erop. Surgery Res. 3:130-138, 1971.
Whittaker et al., "Transmural Channels Can Protect Ischemic Tissue", Circulation 93(1):143-152, Jan. 1, 1996.
EP Search Report for EP01124768 2 pgs, Nov. 30, 2001.
EP Search Report for EP01935650 10 pgs, Mailed Jul. 26, 2006.
EP Search Report for EP01935650 8 pgs, Mailed May 3, 2005.
EP Search Report for EP02768969 3 pgs, Mailed Feb. 12, 2007.
EP Search Report for EP03762238 3 pgs, Mailed Jun. 2, 2006.
EP Search Report for EP94916716 2 pgs, Oct. 29, 1996.
EP Search Report for EP96941386 2 pgs, Nov. 27, 1998.

EP Search Report for EP98952032 2 pgs, Nov. 24, 2000.
PCT International Search Report for PCT/US00/07718 1pg, Mailed Sep. 5, 2000.
PCT International Search Report for PCT/US01/16006 1pg, Mailed Aug. 14, 2001.
PCT International Search Report for PCT/US02/31640 1pg, Mailed May 23, 2003.
PCT International Search Report for PCT/US03/04689 1 pg, Mailed Sep. 26, 2003.
PCT International Search Report for PCT/US03/12790 1 pg, Mailed Aug. 12, 2003.
PCT International Search Report for PCT/US03/20574 1 pg, Mailed May 25, 2005.
PCT International Search Report for PCT/US04/22803 1 pg, Mailed Apr. 29, 2005.
PCT International Search Report for PCT/US05/07038 1 pg, Mailed Sep. 2, 2005.
PCT International Search Report for PCT/US94/05168, 1 pg, Mailed Oct. 18, 1994.
PCT International Search Report for PCT/US98/20768 1pg, Mailed Jan. 20, 1999.
PCT International Search Report for PCT/US98/22327 1 pg, Mailed Feb. 9, 1999.
PCT IPER for PCT/US01/16006 3pgs, Apr. 16, 2002.
PCT IPER for PCT/US98/22327 4pgs, Aug. 27, 2000.
PCT Written Opinion for PCT/US04/22803 3pgs, Mailed Apr. 29, 2005.
PCT Written Opinion for PCT/US05/07038 3pgs, Mailed Sep. 2, 2005.
UK Search Report for GB0805061.9 1 pg, Jul. 15, 2008.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC—III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artheroscleotic Vascular Tissue with Use" JACC vol. 13(5), pp. 1167-1171, 1989.
Letter from Department of Health to Jerry Malis dated Jan. 24, 1991, 3 pgs, Jan. 24, 1991.
Letter from Department of Health to Jerry Malis dated Jul. 25, 1985, 1 pg, Jul. 25, 1985.
Letter from Jerry Malis to FDA dated Jul. 25, 1985, 2 pgs, Jul. 25, 1985.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.

(56) References Cited

OTHER PUBLICATIONS

Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, a Comparison of four endoscopic methods of electrocoagulation in experimental bleeding ulcers" *Gut* vol. 25, pp. 1424-1431, 1987.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder " *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker, R. et al., Abstract P14-11, p. 248, "A Bipolar Electrosurgical Turp Loop", Nov. 1989.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
BiLAP IFU 910033-002 Rev A for BiLAP Model 3527, L-Hook; BiLAP Model 35:25, J-Hook; BiLAP Model 3529, High Angle, 2 pgs, Nov. 30, 1993.
BiLAP IFU 910026-001 Rev A for BiLAP Model 3525, J-Hook, 4 pgs, May 20, 1991.
BiLAP Generator Settings, Jun. 1991.
Tucker et al. "The interaction between electrosurgical generators, endoscopic electrodes, and tissue," Gastrointestinal Endoscopy, vol. 38, No. 2, pp. 118-122, 1992.
EP Search Report for EP 07118068 3pgs, Mailed Dec. 27, 2010.
EP Search Report for EP 04778347 4pgs, Feb. 22, 2011.
UK Search Report for GB0921635.9 3pgs, Apr. 12, 2010.
UK Search Report for GB1106425.0 6 pages, Mailed Aug. 16, 2011.
UK combined Search and Examination Report for GB1121048.1 3pgs, Apr. 18, 2012.

* cited by examiner

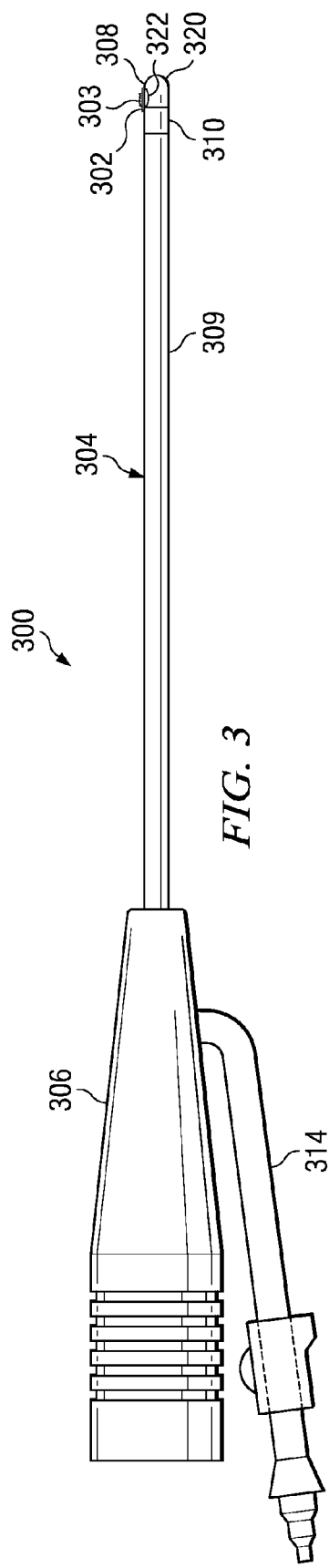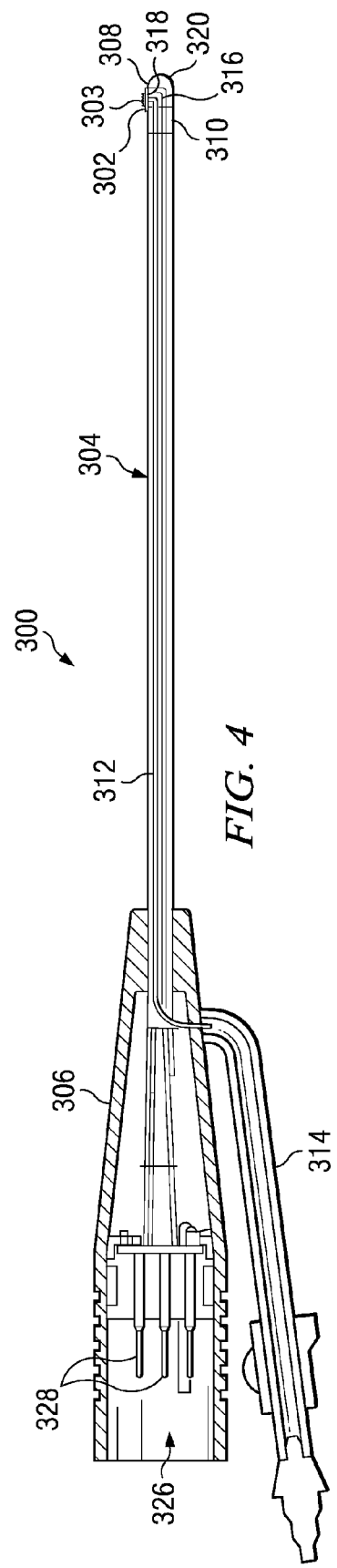

SYSTEMS AND METHODS FOR SCREEN ELECTRODE SECUREMENT

FIELD OF THE INVENTION

The present invention relates generally to the field of electrosurgery, and more particularly to apparatus and methods for applying high frequency voltage to ablate tissue. More particularly, the present invention relates to apparatus and methods for securing a substantially flat screen-type active electrode to the distal tip of the shaft of an electrosurgical instrument.

BACKGROUND OF THE INVENTION

Conventional electrosurgical methods are widely used since they generally achieve hemostasis and reduce patient bleeding associated with tissue cutting operations while improving the surgeon's visibility of the treatment area. Many of the electrosurgical devices used in electrosurgery make use of a screen-type active electrode which is typically cut, or etched, from a sheet of conductive material. These electrosurgical devices and procedures, however, suffer from a number of disadvantages. For example, screen-type active electrodes typically require some method of securement to an insulative body and furthermore to the distal tip of the device itself. Failure to adequately secure the screen electrode to the insulative body may result in improper device function and possible patient harm during the electrosurgical procedure.

Prior attempts to secure the screen active electrode to the insulative body have involved mechanical, thermal, and chemical means or various combinations thereof. Numerous mechanical forms of securement have been utilized, while adhesives have been used as a chemical form of joining, and welding the screen may provide one thermal method of joining. These mechanical joining methods may also include the use of plastic, or non-recoverable, deformations of the materials being used for securement. However, even in combination with other joining methods, the above-listed methods for fixation provide only marginally effective solutions that typically are challenged over extended periods of use.

Accordingly, devices and methods which allow for the securement of flat screen active electrodes to the insulative body of an electrosurgical instrument while maintaining electrical connections through the insulative body are desired. In particular, mechanical methods for providing reasonable and durable securement of an electrically connected screen active electrode to the insulative body at the distal tip of an electrosurgical device while providing enhanced electrosurgical operating parameters are desired.

SUMMARY OF THE INVENTION

The present invention provides systems, apparatus and methods for mechanically securing a screen type active electrode to the insulative body at the distal tip of an electrosurgical device. In particular, methods and apparatus are provided for reliably securing the screen electrode over extended periods of use. Further, the methods and systems of the present invention are particularly useful for providing expanded and enhanced electrosurgical operating parameters.

In one aspect of the invention, the method of securement comprises inserting a securing electrode through a channel or slot in both the screen electrode and insulative body. In a configuration where the screen electrode is supported by the insulative body, the securing electrode functions to mechanically couple the screen electrode to the insulative body, and also functions to electrically couple the screen electrode to a high frequency power supply via electrical connectors. The securing electrode may be characterized by extended leg portions having tabs at one end that engage or interfere with the channel in the insulative body, thereby preventing axial movement of the securing electrode. Thus, the securing electrode provides a mechanical method of joining the screen electrode to the insulative body while also providing an electrical connection to transmit RF energy through the insulative body to the screen electrode.

Another configuration of the electrosurgical device according to the present disclosure comprises an active screen electrode having at least two bilateral channels therethrough. At least two bilateral securing electrodes are provided and are respectively inserted through the channels of the screen electrode. Additionally, the device comprises an insulative support member having at least two bilateral channels correspondingly positioned with regard to the screen electrode channels. The bilateral securing electrodes are inserted through the support member and screen electrode channels and may be oriented symmetrically to thereby allow for creation of a zone for RF ablation between the two securing electrodes. Further, the bilateral screen electrodes each have a leg portion with a tab at one end, wherein the tab slides into a locked position within the support member to secure the screen electrode in place.

In certain configurations, the securing electrodes may be characterized by a saw tooth pattern on a superior surface. Additionally, the securing electrodes may be formed in the shape of a staple or bridge, thereby allowing for the creation of another zone of RF ablation in a space between the staple securing electrode and the screen electrode. The added edges formed on the securing electrode in these configurations may result in increased current density and thus promote the formation of improved zones of RF ablation.

In yet another configuration, the active electrode comprises a conductive screen having a plurality of holes and is positioned over the insulative body at the distal tip of an electrosurgical device in relation to the distal opening of an aspiration lumen. In the representative embodiment, the screen electrode is supported by the insulating support member such that the one of the plurality of holes on the screen is aligned with the aspiration lumen opening, thereby allowing for the aspiration of unwanted tissue and electrosurgery byproducts from the target site. Additionally, the screen and the distal opening of the aspiration lumen may be positioned on a lateral side of the instrument (i.e., facing 90 degrees from the instrument axis).

In open procedures, the system may further include a fluid delivery element for delivering electrically conducting fluid to the active electrode(s) and the target site. The fluid delivery element may be located on the instrument, e.g., a fluid lumen or tube, or it may be part of a separate instrument. Alternatively, an electrically conducting gel or spray, such as a saline electrolyte or other conductive gel, may be applied to the tissue. In addition, in arthroscopic procedures, the target site will typically already be immersed in a conductive irrigant, i.e., saline. In these embodiments, the apparatus may not have a fluid delivery element. In both embodiments, the electrically conducting fluid will preferably provide a current flow path between the active electrode terminal(s) and the return electrode(s). In an exemplary embodiment, a return electrode is located on the instrument and spaced a sufficient distance from the active electrode terminal(s) to substantially avoid or minimize current shorting therebetween and to isolate the return electrode from tissue at the target site.

In another aspect of the invention, a method comprises positioning one or more active electrode(s) (which may include an active screen electrode and securing electrode) at the target site within a patient's body and applying a suction force to a tissue structure to draw the tissue structure to the active electrode(s). High frequency voltage is then applied between the active electrode(s) and one or more return electrode(s) to ablate the tissue structure. Typically, the tissue structure comprises a flexible or elastic connective tissue, such as synovial tissue. This type of tissue is typically difficult to remove with conventional mechanical and electrosurgery techniques because the tissue moves away from the instrument and/or becomes clogged in the rotating cutting tip of the mechanical shaver or microdebrider. The present invention, by contrast, draws the elastic tissue towards the active electrodes, and then ablates this tissue with the mechanisms described above.

BRIEF DESCRIPTION OF THE DRAWINGS

FIG. 3 is a side view of an electrosurgical probe for ablating and removing tissue;

FIG. 4 is a cross-sectional view of the electrosurgical probe of FIG. 3;

DETAILED DESCRIPTION OF THE INVENTION

Figure 1:
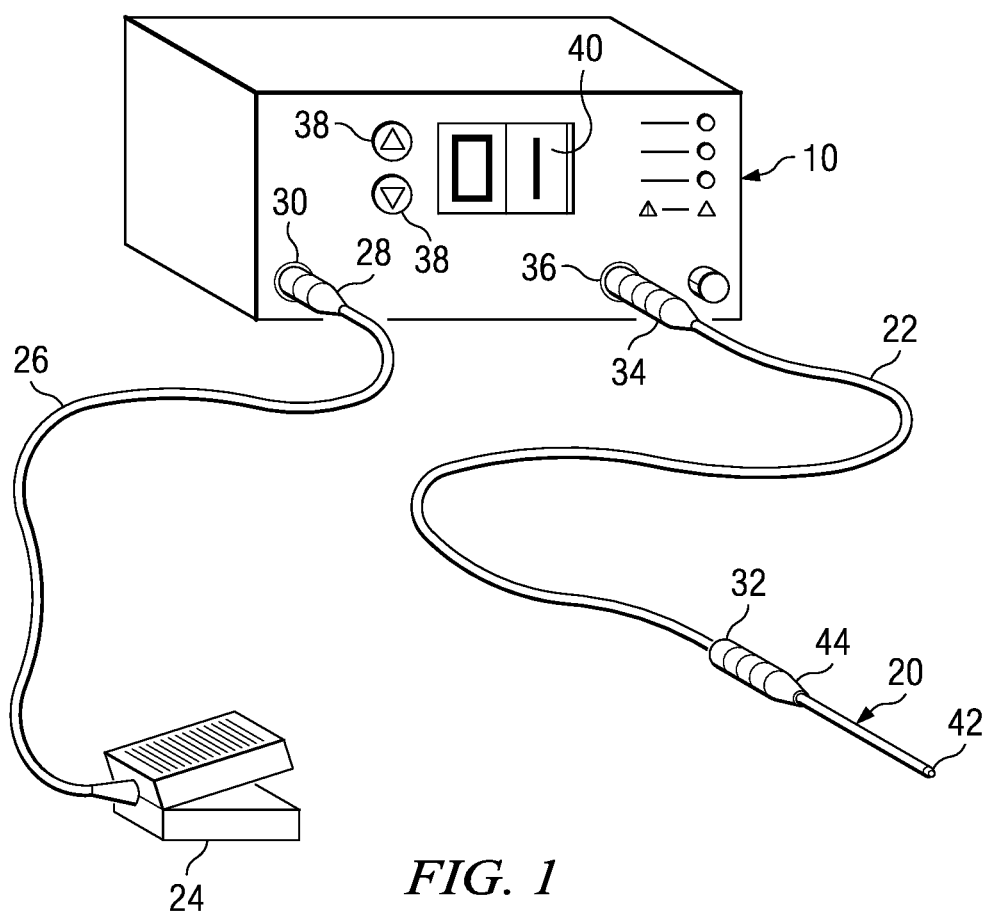
FIG. 1 is a perspective view of an electrosurgical system incorporating a power supply and an electrosurgical probe.

The present invention provides systems and methods for selectively applying electrical energy to a target location within or on a patient's body. The present invention is particularly useful in procedures where the tissue site is flooded or submerged with an electrically conducting fluid, such as arthroscopic surgery of the knee, shoulder, ankle, hip, elbow, hand or foot. In other procedures, the present invention may be useful for collagen shrinkage, ablation and/or hemostasis in procedures for treating target tissue alone or in combination with the volumetric removal of tissue. More specifically, the embodiments described herein provide for electrosurgical devices characterized by a substantially flat screen active electrode disposed at the distal tip of the device. Additionally, the present embodiments include apparatus and methods for the mechanical securement of the screen electrode to the insulative body located at the distal tip of the device. Such methods of mechanical securement of the screen electrode may extend the operating period of the electrosurgical device by providing a more secure method of attachment.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The electrosurgical device of the present embodiments may have a variety of configurations as described above. However, at least one variation of the embodiments described herein employs a treatment device using Coblation® technology.

As stated above, the assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of these phenomena can be found in commonly assigned U.S. Pat. No. 5,697,882 the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of these phenomena can be found in commonly assigned U.S. Pat. Nos. 6,355,032, 6,149,120 and 6,296,136, the complete disclosures of which are incorporated herein by reference.

The active electrode(s) of a Coblation® device may be supported within or by an inorganic insulating support member positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

Further discussion of applications and devices using Coblation® technology may be found as follows. Issued U.S. Pat. Nos. 6,296,638; and 7,241,293 both of which are incorporated by reference. Pending U.S. application Ser. No. 11/612,995 filed Dec. 19, 2006, which is incorporated by reference.

In one example of a Coblation® device for use with the presently-described embodiments, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation® treatment device for use according to the present descriptions may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In certain configurations, each individual active electrode in the electrode array may be electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, in certain embodiments the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation).

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Referring now to FIG. 1, an exemplary electrosurgical system for resection, ablation, coagulation and/or contraction of tissue will now be described in detail. As shown, certain embodiments of the electrosurgical system generally include an electrosurgical probe 20 connected to a power supply 10 for providing high frequency voltage to one or more electrode terminals on probe 20. Probe 20 includes a connector housing 44 at its proximal end, which can be removably connected to a probe receptacle 32 of a probe cable 22. The proximal portion of cable 22 has a connector 34 to couple probe 20 to power supply 10 at receptacle 36. Power supply 10 has an operator controllable voltage level adjustment 38 to change the applied voltage level, which is observable at a voltage level display 40. Power supply 10 also includes one or more foot pedals 24 and a cable 26 which is removably coupled to a receptacle 30 with a cable connector 28. The foot pedal 24 may also include a second pedal (not shown) for remotely adjusting the energy level applied to electrode terminals 42, and a third pedal (also not shown) for switching between an ablation mode and a coagulation mode.

Figure 2:
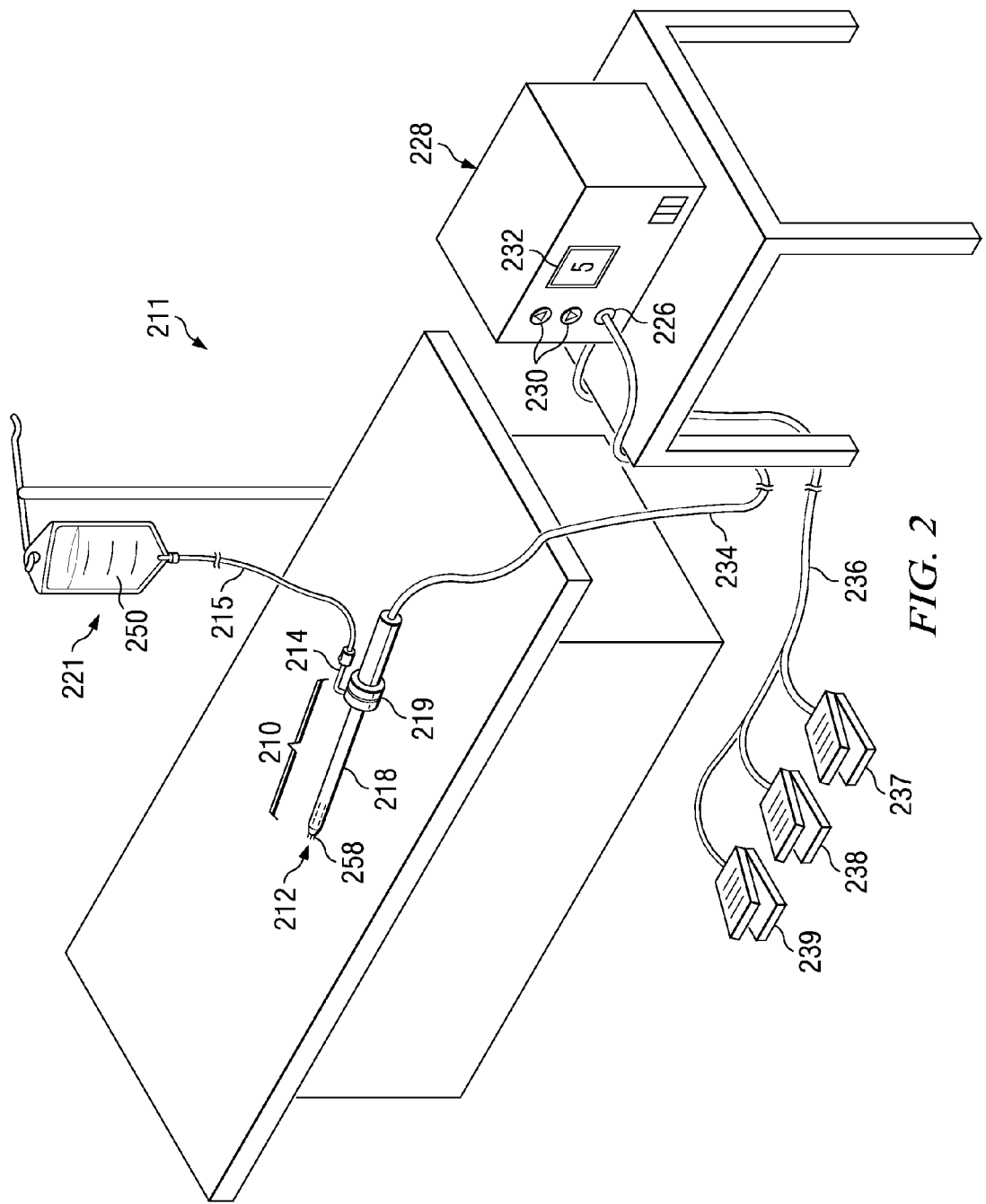
FIG. 2 is a perspective view of another electrosurgical system incorporating a power supply, an electrosurgical probe and a supply of electrically conductive fluid for delivering the fluid to the target site.

Referring now to FIG. 2, an exemplary electrosurgical system 211 for treatment of tissue in 'dry fields' will now be described in detail. Of course, system 211 may also be used in 'wet field', i.e., the target site is immersed in electrically conductive fluid. However, this system is particularly useful in 'dry fields' where the fluid is preferably delivered through electrosurgical probe to the target site. As shown, electrosurgical system 211 generally comprises an electrosurgical handpiece or probe 210 connected to a power supply 228 for providing high frequency voltage to a target site and a fluid source 221 for supplying electrically conducting fluid 250 to probe 210. The system 211 may also include a vacuum source (not shown) for coupling to a suction lumen disposed in probe 210 (not shown) via a connection tube (not shown) on probe 210 for aspirating the target site, as discussed below in more detail.

As shown, probe 210 generally includes a proximal handle 219 and an elongate shaft 218 having an array 212 of electrode terminals 258 at its distal end. A connecting cable 234 has a connector 226 for electrically coupling the electrode terminals 258 to power supply 228. The electrode terminals 258 are electrically isolated from each other and each of the terminals 258 is connected to an active or passive control network within power supply 228 by means of a plurality of individually insulated conductors (not shown). A fluid supply tube 215 is connected to a fluid tube 214 of probe 210 for supplying electrically conducting fluid 250 to the target site.

Similar to the above embodiment shown in FIG. 1, power supply 228 has an operator controllable voltage level adjustment 230 to change the applied voltage level, which is observable at a voltage level display 232. Power supply 228 also includes first, second and third foot pedals 237, 238, 239 and a cable 236 which is removably coupled to power supply 228. The foot pedals 237, 238, 239 allow the surgeon to remotely adjust the energy level applied to electrode terminals 258. In an exemplary embodiment, first foot pedal 237 is used to place the power supply into the "ablation" mode and second foot pedal 238 places power supply 228 into the "coagulation" mode. The third foot pedal 239 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 230 or third foot pedal 239 may be used to adjust the voltage level to adjust the degree or aggressiveness of the ablation.

It will be recognized that the voltage and modality of the power supply may be controlled by other input devices. However, applicant has found that foot pedals are convenient methods of controlling the power supply while manipulating the probe during a surgical procedure.

In the coagulation mode, the power supply 228 applies a low enough voltage to the electrode terminals (or the coagulation electrode) to avoid vaporization of the electrically conductive fluid and subsequent molecular dissociation of the tissue. The surgeon may automatically toggle the power supply between the ablation and coagulation modes by alternatively stepping on foot pedals 237, 238, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 238, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 237.

Now referring to FIGS. 3 and 4, an exemplary electrosurgical probe 300 incorporating an active screen electrode 302 is illustrated. Probe 300 may include an elongated shaft 304 which may be flexible or rigid, a handle 306 coupled to the proximal end of shaft 304 and an electrode support member 308 coupled to the distal end of shaft 304. Probe 300 further includes active screen electrode 302 and securing electrode 303. Return electrode 310 is spaced proximally from screen electrode 302 and provides a method for completing the current path between screen electrode 302 and securing electrode 303. As shown, return electrode 310 preferably comprises an annular exposed region of shaft 304 slightly proximal of insulative support member 308, typically about 0.5 to 10 mm and more preferably about 1 to 10 mm. Securing electrode 303 and return electrode 310 are each coupled to respective connectors 328 disposed in handle 306 (as illustrated in FIG. 4) that extend to the proximal end of probe 300, where connectors 328 are suitably electrically connected to a power supply (e.g., power supply 10 in FIG. 1 or power supply 228 in FIG. 2). As shown in FIG. 4, handle 306 defines an inner cavity 326 that houses the electrical connectors 328, and provides a suitable interface for connection to an electrical connecting cable (e.g., cable 22 in FIG. 1 or cable 234 in FIG. 2).

Still referencing FIGS. 3 and 4, in certain embodiments screen electrode 302, securing electrode 303 and insulative support member 308 are configured such that screen electrode 302 and securing electrode 303 are positioned on a lateral side of the shaft 304 (e.g., 90 degrees from the shaft axis) to allow the physician to access tissue that is offset from the axis of the portal or arthroscopic opening into the joint cavity in which the shaft 304 passes during the procedure. To accomplish this, probe 300 may include an electrically insulating cap 320 coupled to the distal end of shaft 304 and having a lateral opening 322 for receiving support member 308, screen electrode 302, and securing electrode 303.

Shaft 304 preferably comprises an electrically conducting material, usually metal, which is selected from the group consisting of tungsten, stainless steel alloys, platinum or its alloys, titanium or its alloys, molybdenum or its alloys, and nickel or its alloys. Shaft 304 may include an electrically insulating jacket 309, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure and an exposed electrode could result in unwanted heating and necrosis of the structure at the point of contact causing necrosis.

The probe 300 further includes a suction connection tube 314 for coupling to a source of vacuum, and an inner suction lumen 312 (FIG. 4) for aspirating excess fluids, tissue fragments, and/or products of ablation (e.g., bubbles) from the target site. Preferably, connection tube 314 and suction lumen 312 are fluidly connected, thereby providing the ability to create a suction pressure in lumen 312 that allows the surgeon to draw loose tissue, e.g., synovial tissue, towards the screen electrode 302. Typically, the vacuum source is a standard hospital pump that provides suction pressure to connection tube 314 and lumen 312. As shown in FIGS. 3 and 4, internal suction lumen 312, which preferably comprises peek tubing, extends from connection tube 314 in handle 306, through shaft 304 to an axial opening 316 in support member 308, through support member 308 to a lateral opening 318 in support member 308. Lateral opening 318 is positioned adjacent to screen electrode 302, which further includes a suction port (not shown) disposed on the surface of screen electrode 302 and fluidly connected to lateral opening 318 for allowing aspiration therethrough, as discussed below in more detail.

Figure 5:
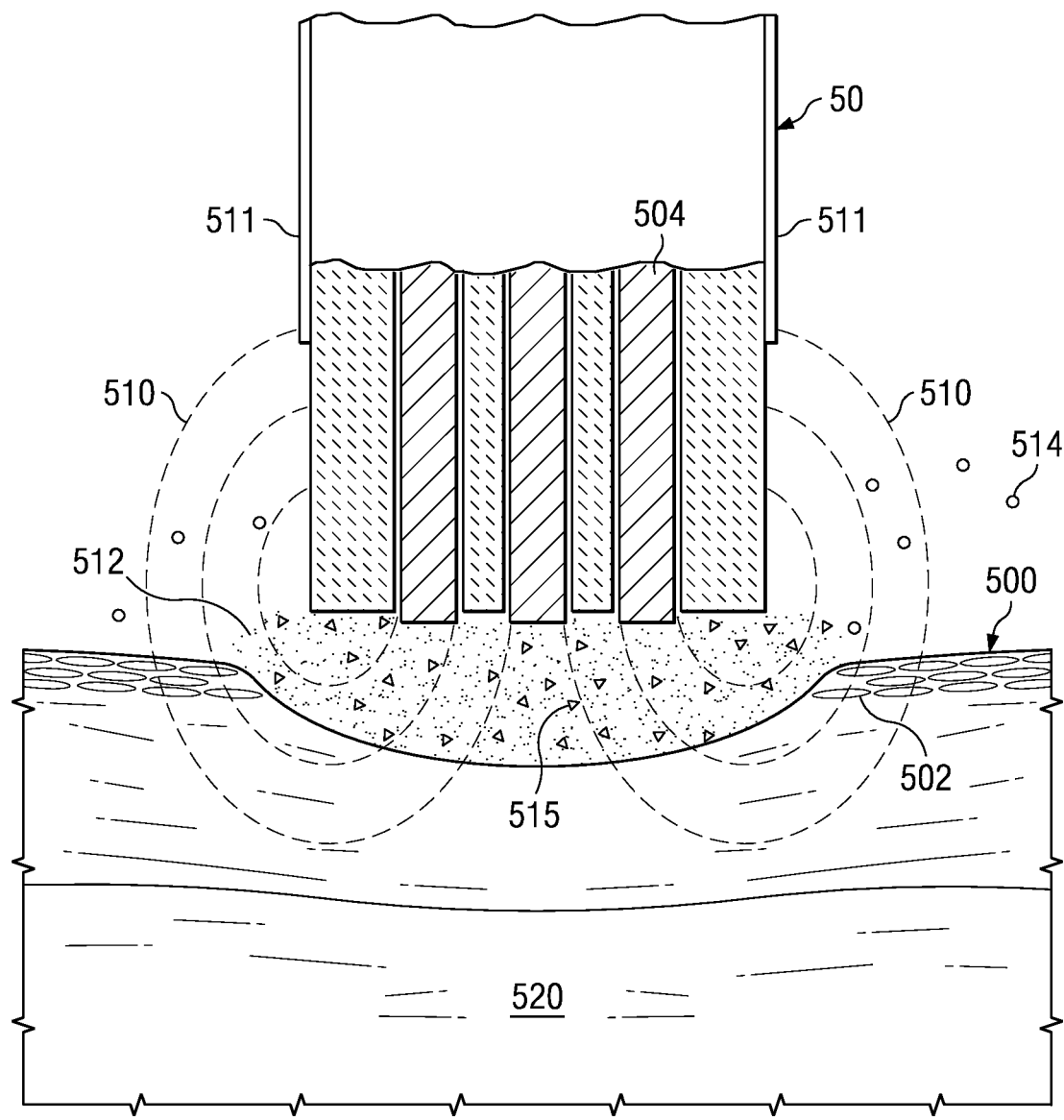
FIG. 5 illustrates a detailed view illustrating ablation of tissue.

FIG. 5 representatively illustrates in more detail the removal of a target tissue by use of an embodiment of electrosurgical probe 50 according to the present disclosure. As shown, the high frequency voltage is sufficient to convert the electrically conductive fluid (not shown) between the target tissue 502 and active electrode terminal(s) 504 into an ionized vapor layer 512 or plasma. As a result of the applied voltage difference between electrode terminal(s) 504 and the target tissue 502 (i.e., the voltage gradient across the plasma layer 512), charged particles 515 in the plasma are accelerated. At sufficiently high voltage differences, these charged particles 515 gain sufficient energy to cause dissociation of the molecular bonds within tissue structures in contact with the plasma field. This molecular dissociation is accompanied by the volumetric removal (i.e., ablative sublimation) of tissue and the production of low molecular weight gases 514, such as oxygen, nitrogen, carbon dioxide, hydrogen and methane. The short range of the accelerated charged particles 515 within the tissue confines the molecular dissociation process to the surface layer to minimize damage and necrosis to the underlying tissue 520.

During the process, the gases 514 will be aspirated through a suction opening and suction lumen to a vacuum source (not shown). In addition, excess electrically conductive fluid, and other fluids (e.g., blood) will be aspirated from the target site 500 to facilitate the surgeon's view. During ablation of the tissue, the residual heat generated by the current flux lines 510 (typically less than 150° C.) between electrode terminals 504 and return electrode 511 will usually be sufficient to coagulate any severed blood vessels at the site. If not, the surgeon may switch the power supply (not shown) into the coagulation mode by lowering the voltage to a level below the threshold for fluid vaporization, as discussed above. This simultaneous hemostasis results in less bleeding and facilitates the surgeon's ability to perform the procedure. Once the blockage has been removed, aeration and drainage are reestablished to allow the sinuses to heal and return to their normal function.

Figure 6:
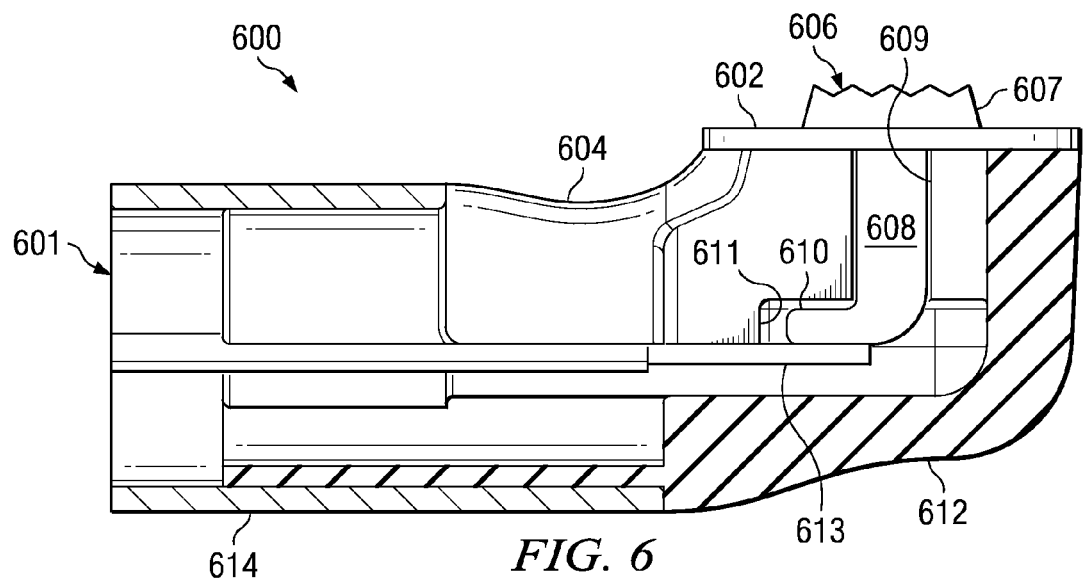
FIG. 6 is an enlarged detailed view of the distal end portion of an embodiment of the probe of FIG. 3.

Now referring to FIG. 6, the distal end portion of a preferred embodiment of an electrosurgical probe according to present disclosure is shown. Electrosurgical probe 600 comprises active screen electrode 602 mounted to insulative support member 604 disposed at a distal end of elongate shaft 601. Probe 600 also includes electrically insulating cap 612 coupled to the end of shaft 601 and configured to receive screen electrode 602 and support member 604. In preferred embodiments, securing electrode 606 extends through screen electrode 602 and support member 604 to mechanically secure screen electrode 602 to support member 604 and electrically insulating cap 612. In certain configurations, securing electrodes 606 may be characterized by head 607, leg 608, and tab 610. Preferably, head 607 contacts or engages the superior surface of screen electrode 602, thereby providing an electrical means for the transmission of RF energy between securing electrode 606 and screen electrode 602. Support member 604 may be characterized by channel 609 and slot 611, wherein channel 609 is oriented perpendicularly with respect to the axis of shaft 601 and slot 611 is oriented axially with respect to the axis of shaft 601. Wire 613 extends proximally from slot 611, and is electrically connected to the electrical connectors disposed in the handle of the probe (as discussed above). Return electrode 614 is spaced proximally from screen electrode 602. As discussed above, in this embodiment screen electrode 602 and support member 604 are configured such that screen electrode 602 is positioned on the lateral side of shaft 601 (e.g., 90 degrees from the shaft axis) to allow the physician to access tissue that is offset from the axis of the port or arthroscopic opening into the joint cavity in which shaft 601 passes during the procedure.

Figure 7A:
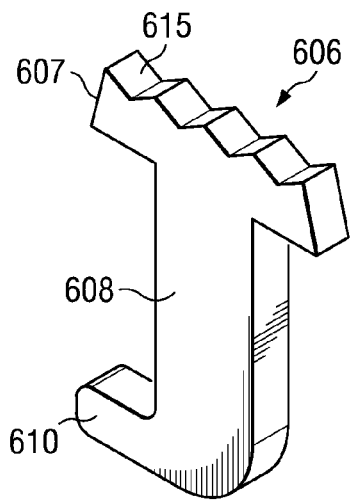
FIGS. 7A and 7B are detailed view of the securing electrode and screen electrode utilized in the electrosurgical probe of FIG. 6.

Referring now to FIG. 7A, an embodiment of securing electrode 606 is shown. Securing electrode 606 may be formed with a conductive material such as tungsten, and the shape and profile of securing electrode 606 may be manufactured via etching, laser cutting, or injection molding. In certain configurations, securing electrode 606 may be characterized by saw tooth pattern 615 on the superior plasma forming surface of securing electrode 606. The added edges formed on securing electrodes 606 by saw tooth pattern 615 in this configuration may result in increased current density and thus promote the formation of improved zones for plasma formation and RF ablation.

Figure 7B:
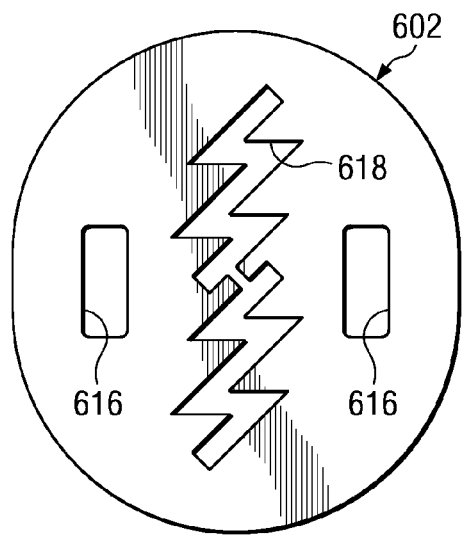

Referring now to FIG. 7B, screen electrode 602 will comprise a conductive material, such as tungsten, titanium, molybdenum, stainless steel, aluminum, gold, copper or the like. Screen electrode 602 will usually have a diameter in the range of about 0.5 to 8 mm, preferably about 1 to 4 mm, and a thickness of about 0.05 to about 2.5 mm, preferably about 0.1 to 1 mm. Screen electrode 602 may have a variety of different shapes, such as the shape shown in FIG. 7B. Screen electrode may have slots 616 therethrough, and may comprise suction opening 618 having sizes and configurations that may vary depending on the particular application. Suction opening 618 will typically be large enough to allow ablated tissue fragments to pass through into suction lumen port 620 (see FIG. 8), typically being about 2 to 30 mils in diameter, preferably about 5 to 20 mils in diameter. In some applications, it may be desirable to only aspirate fluid and the gaseous products of ablation (e.g., bubbles) so that the holes may be much smaller, e.g., on the order of less than 10 mils, often less than 5 mils. In certain configurations, suction opening 618 may be formed in the shape of a zigzag or lightning bolt.

Figure 8:
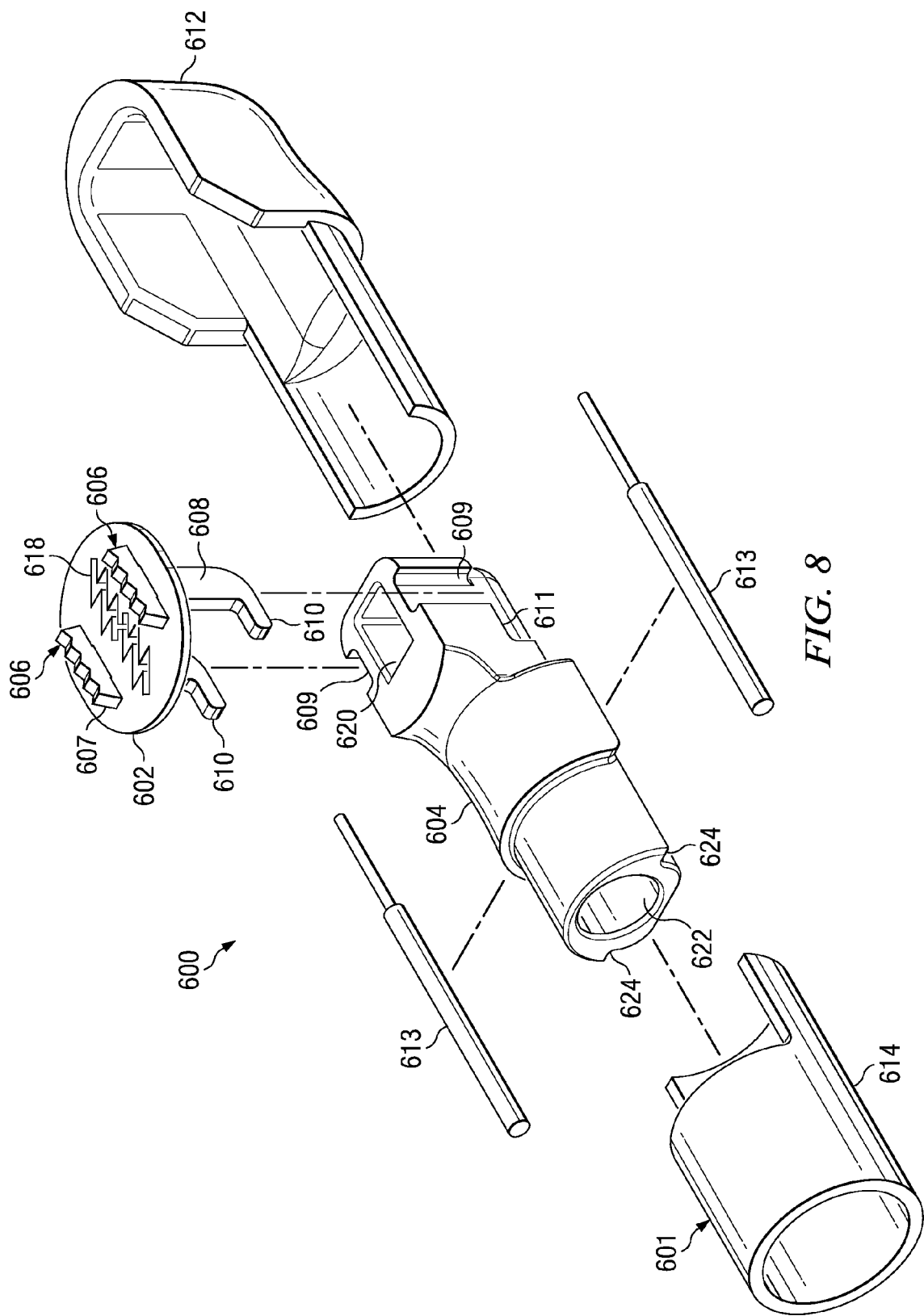
FIG. 8 is an exploded view of the distal end portion of the probe of FIG. 6.

Referring now to FIG. 8, insulative electrode support member 604 preferably comprises an inorganic material, such as glass, ceramic, silicon nitride, alumina or the like, that has been formed with lateral and axial suction lumen openings 620, 622, and with one or more lateral axial passages 624 for receiving electrical wires 613. Wires 613 extend from electrical connectors (i.e., electrical connectors 328 in FIG. 4), through shaft 601 and passages 624 in support member 604, terminating in proximity to slots 611 and tabs 610 of securing electrodes 606. Wires 613 are electrically connected to securing electrodes 606 (e.g., by a laser welding process) thereby electrically coupling securing electrodes 606 and screen electrode 602 to a high frequency power supply. Referring to FIGS. 6, 7B, and 8, legs 608 may extend through slots 616 of screen electrode 602 and channels 609 of support member 604, and tabs 610 may be inserted into slots 611 of support member 604 such that tabs 610 interfere or engage with a portion of support member 604. The placement of securing electrodes 606 such that tabs 610 are inserted into slots 611 creates a mechanical method of joining securing electrodes 606 to support member 604 and thereby prevents securing electrodes 606 from moving axially with respect to shaft 601 and support member 604. Additionally, the method of mechanical securement results in the capture of screen electrode 602 between securing electrodes 606 and support member 604. Further, as described above the contact between heads 607 of securing electrodes 606 and screen electrode 602 provides a method to electrically transmit RF energy through support member 604 to screen electrode 602.

In additional embodiments, the mechanical method of joining may comprise complementary helical threads cut in channels 609 of support member 604 and respectively in legs 608 of securing electrodes 606, wherein legs 608 of securing electrodes 606 are operable to threadingly engage channels 609 of support member 604. Additional embodiments of the present disclosure may include configurations where tabs 610 are formed in a barb or arrowhead shape and are disposed in interference with support member 604. Moreover, in additional embodiments tabs 610 may be completely enclosed within support member 604, and may be further secured to support member 604 by epoxy.

Figure 9:
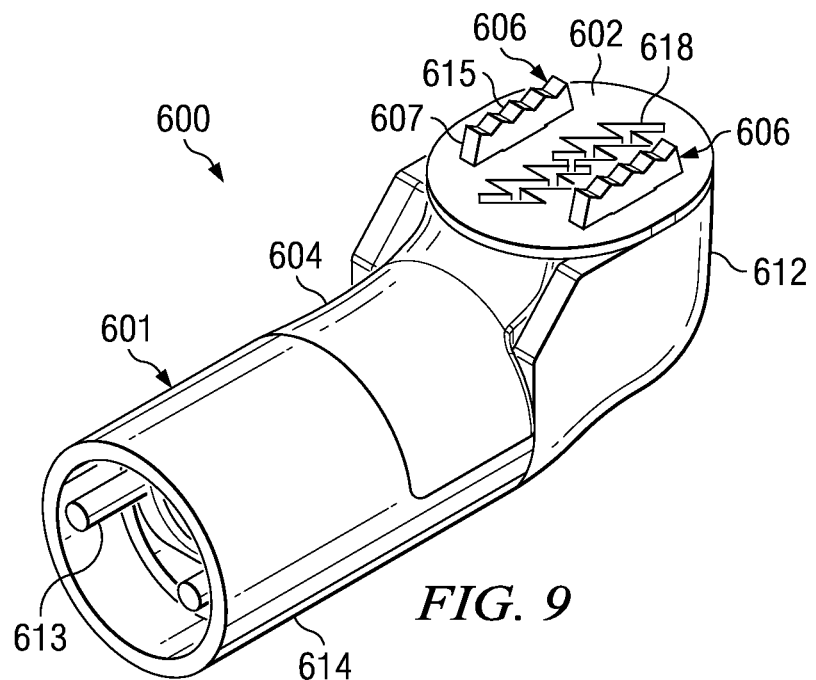
FIG. 9 is a perspective view of the distal end portion of the probe of FIG. 6.
Figure 10:
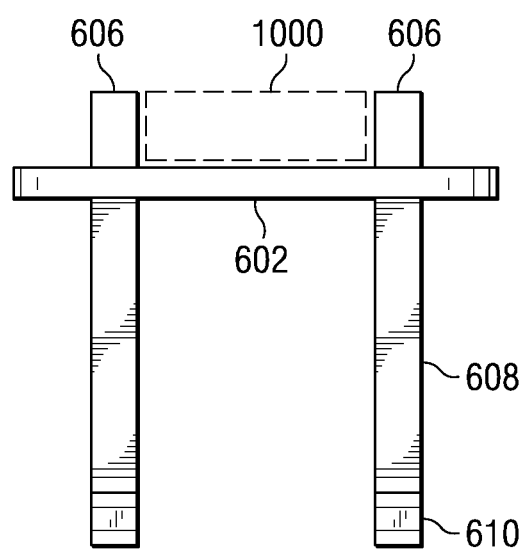
FIG. 10 is a perspective view of the securing electrodes and screen electrode.

Referring now to FIGS. 9 and 10, the distal end portion of representative probe 600 is shown with at least two bilateral securing electrodes 606 thereon. In this configuration, securing electrodes 606 may be oriented symmetrically about the central axis of shaft 601, and may thereby allow for creation of a zone for RF ablation or plasma chamber 1000 between the symmetrically oriented bilateral securing electrodes 606 as well as between securing electrodes 606 and screen electrode 602 (see i.e., FIG. 10). Incorporation of symmetrical securing electrodes 606 may allow for the creation of a three dimensional zone represented by plasma zone 1000 for carrying out RF ablation.

Other modifications and variations can be made to disclose embodiments without departing from the subject invention as defined in the following claims. For example, it should be noted that the invention is not limited to an electrode array comprising a plurality of electrode terminals. The invention could utilize a plurality of return electrodes, e.g., in a bipolar array or the like. In addition, depending on other conditions, such as the peak-to-peak voltage, electrode diameter, etc., a single electrode terminal may be sufficient to contract collagen tissue, ablate tissue, or the like.

In addition, the active and return electrodes may both be located on a distal tissue treatment surface adjacent to each other. The active and return electrodes may be located in active/return electrode pairs, or one or more return electrodes may be located on the distal tip together with a plurality of electrically isolated electrode terminals. The proximal return electrode may or may not be employed in these embodiments. For example, if it is desired to maintain the current flux lines around the distal tip of the probe, the proximal return electrode will not be desired.

While preferred embodiments of this invention have been shown and described, modifications thereof can be made by one skilled in the art without departing from the scope or teaching herein. The embodiments described herein are exemplary only and are not limiting. Because many varying and different embodiments may be made within the scope of the present teachings, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical instrument for removing tissue from a target site within or on a patient's body comprising:
    a shaft having a proximal end and a distal end portion;
    an electrode assembly comprising a substantially flat active screen electrode positioned on the distal end portion of the shaft, at least one return electrode positioned on the shaft and spaced away from the active electrode, and at least one securing electrode positioned on the distal end portion of the shaft and disposed through a screen slot in the screen electrode, the at least one securing electrode comprising an electrode head that electrically connects the at least one securing electrode to the screen electrode;
    wherein the at least one securing electrode further comprises a leg extending from the electrode head, and a tab extending from the leg;
    an electrically insulating support member upon which the screen electrode is mounted, the support member mechanically interfering with and engaging a portion of the tab of the at least one securing electrode, wherein the electrode head has an elongate surface extending beyond the screen slot such that the combination of the electrode head and the tab mechanically act to fixedly secure the screen electrode to the support member and maintain electrical connection between the at least one securing electrode and the screen electrode; and
    at least one electrical connector extending through the shaft, wherein the at least one securing electrode is electrically coupled to the at least one electrical connector at the tab.

2. The instrument of claim 1, wherein the tab mechanically engages a corresponding axial slot disposed along an outer surface of the support member.

3. The instrument of claim 2, wherein the leg is received within a corresponding channel disposed along the outer surface of the support member.

4. The instrument of claim 3, wherein the electrode head engages a superior surface of the active screen electrode, and the leg is received into the corresponding channel through the screen electrode slot.

5. The instrument of claim 1, the at least one securing electrode having a saw tooth pattern on a superior surface.

6. The instrument of claim 1 further comprising an aspiration lumen within the shaft having a distal opening coupled to the screen electrode to inhibit clogging of the lumen, wherein the support member has an axial opening in communication with the lumen and a lateral opening in contact with the screen electrode.

7. The instrument of claim 1 wherein the screen electrode and the at least one securing electrode are configured to be brought adjacent a tissue structure immersed in electrically conductive fluid and the electrically conductive fluid completes a conduction path between the screen electrode, the at least one securing electrode and the return electrode.

8. The instrument of claim 7, wherein upon the application of a sufficiently high frequency voltage between the screen electrode, the at least one securing electrode, and the return electrode the conductive fluid vaporizes in a thin layer over at least a portion of the screen electrode and the at least one securing electrode and induces the discharge of energy from the vapor layer.

9. The instrument of claim 8 wherein the discharge of energy from the vapor layer is sufficient to form a plasma.

10. The instrument of claim 8, wherein the vapor layer is configured to contact the tissue structure and is capable of ablating a portion of the tissue structure.

11. An electrosurgical instrument for removing tissue from a target site within or on a patient's body comprising:
   a shaft having proximal and distal end portions;
   an electrode assembly on the distal end portion, the electrode assembly comprising a substantially flat active screen electrode, a return electrode spaced from the active screen electrode, and bilateral securing electrodes electrically coupled to the active screen electrode and securing the active screen electrode to the shaft;
   wherein each securing electrode comprises an electrode head, a leg extending from the head and a tab extending from the leg, wherein the electrode head has an elongate surface that engages and secures the screen electrode, and wherein the electrode head electrically connects each securing electrode to the screen electrode;
   an insulative support body operable to support the active screen electrode and engage the tabs of the bilateral securing electrodes so as cooperate with the electrode head to mechanically secure the screen electrode to the support body; and
   electrical connectors extending through the shaft, the electrical connectors operable to couple the bilateral securing electrodes with a high frequency power supply.

12. The instrument of claim 11 wherein the tabs engage axial slots in the support body.

13. The instrument of claim 11 wherein the bilateral securing electrodes each have a superior surface characterized by a plurality of teeth.

14. The instrument of claim 11, wherein the bilateral securing electrodes are disposed in a symmetric orientation to one another about a central axis of the shaft.

15. The instrument of claim 14, wherein the symmetric orientation of the bilateral securing electrodes defines a plasma chamber between the bilateral securing electrodes.

* * * * *